United States Patent [19]
Martel et al.

[11] 3,940,354
[45] Feb. 24, 1976

[54] CEPHALOSPORAN COMPOUNDS
[75] Inventors: Jacques Martel, Bondy; René Heymès, Romainville; André Lutz, Strasbourg, all of France
[73] Assignee: Roussel-UCLAF, Paris, France
[22] Filed: Jan. 25, 1974
[21] Appl. No.: 436,502

[30] Foreign Application Priority Data
Jan. 31, 1973 France .............................. 73.03315

[52] U.S. Cl. .......... 260/243 C; 260/243 R; 260/470; 260/483; 424/200; 424/202; 424/230; 424/246
[51] Int. Cl.[2] ....................................... C07D 501/18
[58] Field of Search ................................. 260/243 C

[56] References Cited
UNITED STATES PATENTS
3,867,379  2/1975  Dolfini et al. .................... 260/243 C Primary Examiner—Richard J. Gallagher
Assistant Examiner—Anne Marie T. Tighe
Attorney, Agent, or Firm—Hammond & Littell

[57] ABSTRACT
Cephalosporon compounds of the formula

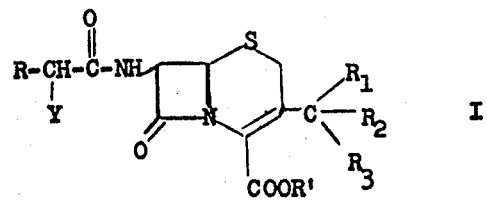

in the form of racemic mixtures or optically active isomers or in the form of their cis or trans isomers or mixtures thereof wherein R is selected from the group consisting of phenyl substituted with at least one hydroxyl and sydnone optionally substituted with phenyl, R' is selected from the group consisting of hydrogen and R'', R'' is an ester group easily removable by acid hydrolysis or hydrogenolysis, $R_1$ and $R_2$ are alkyl of 1 to 3 carbon atoms, $R_3$ is selected from the group consisting of hydrogen and alkyl of 1 to 3 carbon atoms, Y is selected from the group consisting of amino and Y', Y' is hydrogen and NHCOOZ, Z is straight or branched alkyl of 1 to 5 carbon atoms and their non-toxic, pharmaceutically acceptable addition salts with organic and inorganic acids and bases where appropriate with the proviso that when Y is amino, R' is hydrogen and when Y is amino or NHCOOZ, R is phenyl which have antibacterial activity and their preparation.

4 Claims, No Drawings

CEPHALOSPORAN COMPOUNDS

STATE OF THE ART

Copending, commonly assigned U.S. patent application Ser. No. 320,493 filed Jan. 2, 1973 describes desacetoxycephalosporan compounds in which the amino group is substituted with a phenylacetyl group in which the phenyl is optionally substituted with amino, halogen or nitro.

OBJECTS OF THE INVENTION

It is an object of the invention to provide the novel cephalosporan compounds of formula I and their non-toxic, pharmaceutically acceptable salts thereof.

It is a further object of the invention to provide a novel process for the preparation of compounds of formula I.

It is another object of the invention to provide novel antibacterial compositions and to a novel method of combatting bacterial infections in warm-blooded animals.

These and other objects and advantages of the invention will become obvious from the following detailed description.

THE INVENTION

The novel products of the invention are selected from the group consisting of cephalosporan compound of the formula

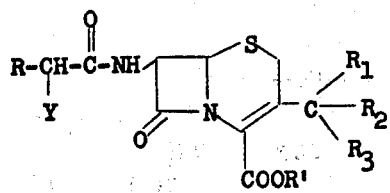

in the form of racemic mixtures or optically active isomers or in the form of their cis or trans isomers or mixtures thereof wherein R is selected from the group consisting of phenyl substituted with at least one hydroxyl and sydnone optionally substituted with phenyl, R' is selected from the group consisting of hydrogen and R'', R'' is an ester group easily removable by acid hydrolysis or hydrogenolysis, $R_1$ and $R_2$ are alkyl of 1 to 3 carbon atoms, $R_3$ is selected from the group consisting of hydrogen and alkyl of 1 to 3 carbon atom, Y is selected from the group consisting of amino and Y', Y' is hydrogen and NHCOOZ, Z is straight or branched alkyl of 1 to 5 carbon atoms and their non-toxic, pharmaceutically acceptable addition salts with organic and inorganic acids and bases where appropriate with the proviso that when Y is amino, R' is hydrogen and when Y is amino or NHCOOZ, R is phenyl. The ester groups easily removable by acid hydrolysis or by hydrogenolysis may be straight or branched alkyl of 1 to 6 carbon atoms optionally substituted with at least one chlorine such as methyl, trichloroethyl or tert.-butyl or aralkyl of 7 to 15 carbon atoms such as benzyl, α-methylbenzyl, p-methylbenzyl or p-methoxybenzyl. $R_1$, $R_2$ and $R_3$ may be alkyl such as methyl, ethyl or propyl and Z may be alkyl such as methyl or tert.-butyl.

Among the preferred compounds of the invention are the compounds of formula I in which R' is hydrogen and Y is amino or hydrogen and their salts. $R_1$ and $R_2$ are preferably methyl and $R_3$ is hydrogen in the most preferred group as well as their salts. Examples of specific compounds are [2'R, 6R, 7R] 7-(α-amino-p-hydroxyphenylacetamido)-3-isopropyl-3-cepheme-4-carboxylic acid and its non-toxic, pharmaceutically acceptable salts and [6R, 7R] 7-(4-phenyl-3-sydnoneacetamido)-3-isopropyl-3-cepheme-4-carboxylic acid and its non-toxic, pharmaceutically acceptable salts.

The novel process of the invention for the preparation of the compounds of formula I comprises reacting a compound of the formula

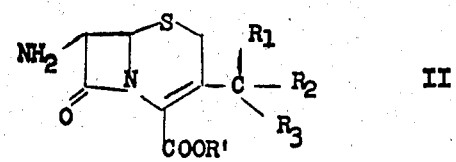

or its acid addition salt with an acid of the formula

or an functional derivative thereof wherein R, $R_1$, $R_2$, $R_3$ and R' have the above definitions and Y' is hydrogen or NHCOOZ to obtain the corresponding compound of formula I wherein Y is other than amino. When R' is hydrogen, the compound may then be esterified or salified to obtain the corresponding esters and salts of formula I. When R' is other than hydrogen or when Y' is NHCOOZ, the product may be subjected to acid hydrolysis or hydrogenolysis to obtain the compound of formula I in which R' is hydrogen and Y is an amino if Y' was NHCOOZ or Y is hydrogen if Y' was hydrogen. The product may be esterified or salified, if desired.

In a preferred mode of the invention, the functional derivative of the acid of formula III is the acid chloride or the acid anhydride which can be formed in situ by action of dicyclohexylcarbodiimide on the acid. Other acid halides or other acid anhydrides formed in situ by reaction with other dicycloalkylcarbodiimides or dialkylcarbodiimides on the acid may also be used. Also useful are acid azides, acid amides or acid esters.

When the reaction of a compound of formula II is reacted with acid halide of formula III, the reaction is preferably effected in the presence of a basic agent such as an alkali metal carbonate or a tertiary organic base such as pyridine or dialkylamine. When the amine of the compound of formula II is salified with a mineral or organic acid, the compound of formula II is reacted with the product of formula III or its functional derivatives in the presence of a basic agent such as an alkali metal carbonate or an organic tertiary base like trialkylamine or pyridine.

As agent for acid hydrolysis of the group COOR', hydrochloric acid is preferably used in admixture with acetic acid. The hydrogenolysis agent is a reducing agent such as a zinc-acetic acid system. The preferred acid hydrolysis agent is trifluoroacetic acid.

The products of formula I in which R' is hydrogen may be esterified by known methods such as reaction with an alcohol in the presence of an acid or may be salified with an organic or mineral base such as sodium hydroxide, potassium hydroxide, diethylamine, triethylamine or dicyclohexylamine.

The products of formula I wherein Y is amino may be salified by known methods with a mineral or organic acid. Examples of suitable mineral acids are hydrohalic acids, sulfuric acid, nitric acid, boric acid or phosphoric acid and examples of organic acids are formic acid, acetic acid, succinic acid, salicylic acid or p-toluene sulfonic acid. The salifications are preferably effected in the presence of at least one solvent such as water, ether, ethanol or acetone.

The compounds of formula II can be prepared by a process analogous to that described in Belgium Pat. No. 793,448 which comprises reacting an epoxide of the formula

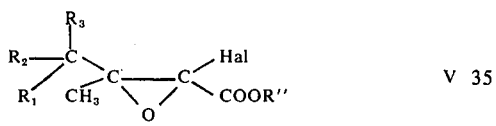
V wherein $R_1$, $R_2$, $R_3$ and $R''$ have the above definitions, and Hal is chlorine or bromine with a reagent capable of dehydrohalogenating the molecule such as lithium bromide or silver nitrate to form an ester of the formula

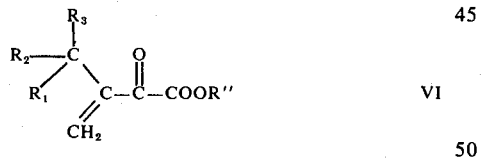
VI reacting the latter in the presence of a weakly basic tertiary amine such as triethylamine with a thioaminal of the formula

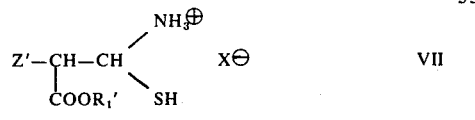
VII wherein Z' is an imidocyclic group which may be substituted, benzoylamino or thiobenzoylamino, $R'_1$ is straight or branched alkyl of 1 to 10 carbon atoms or aralkyl of 7 to 15 carbon atoms and X is a halogen, sulfuric or sulfonic anion to obtain a 2,3-dihydro-1,3-thiazine of the formula

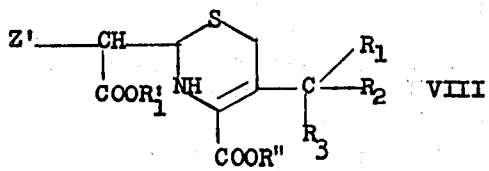
VIII in the form of its threo or erythro isomer or a mixture thereof, reacting the latter with hydrazine or subjecting it to hydrogenolysis to obtain a thiazine of the formula

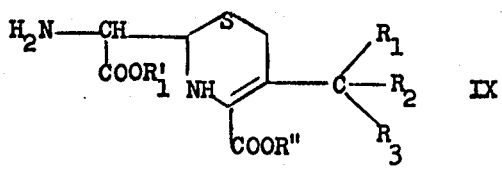
IX in the form of its threo or erythro isomer or a mixture thereof, selectively saponifying the latter with a basic agent such as sodium hydroxide to obtain a compound of the formula

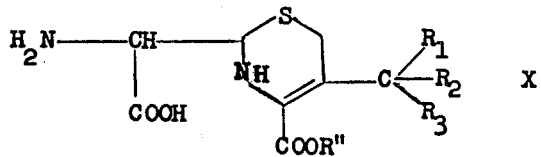
X in the form of its threo or erythro isomer or a mixture thereof, reacting the latter with trityl chloride to obtain a compound of the formula

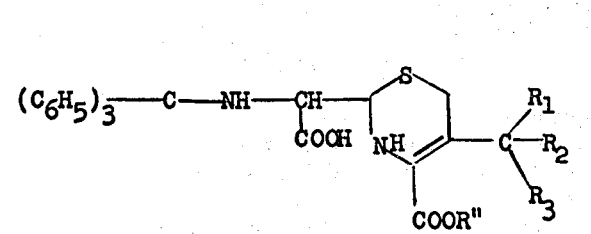

XI in the form of its erythro or threo isomer or a mixture thereof, subjecting the latter to cyclization by action with a lactamization agent such as dicyclohexylcarbodiimide to obtain a compound of the formula

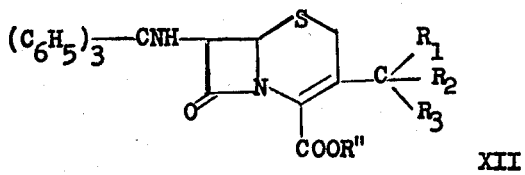
XII in the form of its trans or cis isomer or a mixture thereof, and reacting the latter either with an acid agent under mild conditions such as cold dilute hydrochloric acid to obtain a compound of the formula

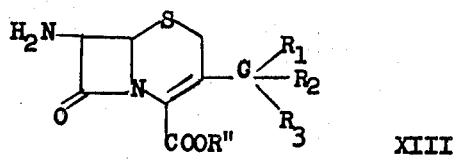
XIII corresponding to a compound of formula II where R' is R'' in the form of its cis or trans isomer or a mixture thereof or with an acid under severe conditions such as gaseous hydrochloric acid to obtain a compound of the formula

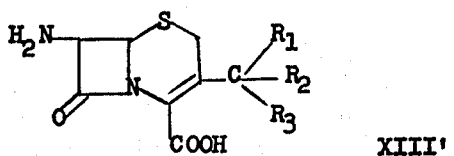
XIII' corresponding to a compound of formula II in which R' is hydrogen in the form of its cis or trans isomer or a mixture thereof.

The α-haloepoxides of formula V may be prepared by a process analogous to that described by Darzens [C.R. Acad. Sci., Vol. 151 (1910), p. 203 & 883] and the thioaminals of formula VII may be prepared by an analogous procedure described in French Pat. No. 2,130,800.

The novel antibiotic compositions of the invention are comprised of at least one compound of formula I and their non-toxic, pharmaceutically acceptable salts thereof where appropriate and a pharmaceutical carrier. The compositions may be in the form of injectable solutions or suspensions, sterile powders for extemperaneous injectable preparation, tablets, coated tablets, gelules, capsules, syrups, suppositories, creams, pomades and aerosol preparation prepared by known methods.

The compositions may also contain other compatible medicants for the treatment of staphylococcia such as septicemia of staphylococcus, malignant staphylococcus on the face or skin, pyodermitis, septic and suppurantis plaies, anthrax, phlegmons, eresipelis, primitive or post-grip acute staphylococcia, bronchopneumonia, pulmonary suppurations and colibacillosis.

Among the preferred products are [2'R, 6R, 7R] 7-(α-amino-p-hydroxyphenylacetamido)-3-isopropyl-3-cepheme-4-carboxylic acid and [6R, 7R] 7-(4-phenyl-3-sydnoneacetamido)-3-isopropyl-3-cepheme-4-carboxylic acid and their salts which possess good antibiotic activity against gram positive bacteria such as staphylococcus, streptococcus and especially penicillin-resistant staphylococcus and certain gram negative bacteria such as coliform bacteria.

The novel method of the invention for combatting bacterial infections in warm-blooded animals comprises administering to warm-blooded animals a safe but antibacterially effective amount of at least one compound of formula I or their non-toxic, pharmaceutically acceptable salts. The compounds may be administered orally, parenterally, rectally or locally by topical application to the skin or mucous membranes. The usual effective daily dose is 20 to 80 mg/kg depending on the compound.

In the following examples there are described several preferred embodiments to illustrate the invention. However, it is to be understood that the invention is not intended to be limited to the specific embodiments.

EXAMPLE 1

αR-tertbutoxycarboxamido-p-hydroxyphenylacetic acid

STEP A: Racemic

α-tertbutoxycarboxamido-p-hydroxyphenylacetic acid 10.65 g of magnesia and 37.8 g of tert.butyl azidoformate were added to a suspension of 22.05 g of racemic α-amino-p-hydroxyphenylacetic acid in a mixture of 275 ml of dioxane and 275 ml of water and after stirring for 20 hours at 40°C, the mixture was filtered to remove solids. The filtrate was diluted with water and was washed with ethyl acetate. The resulting organic phase was washed with an aqueous sodium bicarbonate solution and the combined aqueous phases were acidified with an aqueous citric acid solution. The mixture was extracted with ethyl acetate and the organic extracts were dried over magnesium sulfate and evaporated to dryness to obtain an oil. The oil was taken up in a mixture of ether and petroleum ether (B.p. = 40°–75°C) and the resulting crystals were recovered by vacuum filtration. The crystals were dissolved in ether and the ether solution was added to 8.2 ml of diethylamine to form the diethylamine salt of racemic α-tert.butoxycarboxamido-p-hydroxyphenylacetic acid in the form of crystals which after crystallization from a methanol-isopropyl ether mixture melted at 150°C with decomposition. The said salt was reacted with hydrochloric acid to obtain 15.7 g of the free acid in the form of colorless crystals melting at 100°C, then 135°C (with decomposition).

Analysis: $C_{13}H_{17}NO_5$, Calculated: %C; 58.42, %H; 6.41 %N; 5.24, Found: %C; 58.7, %H; 6.5, %N; 5.1.

STEP B:
αR-tert.butoxycarboxamido-p-hydroxyphenylacetic acid 13 g of racemic α-tert.butoxycarboxamido-p-hydroxyphenylacetic acid were added to a solution of 19 g of natural yohimbine in 63 ml of ethanol and after stirring the mixture for 5 hours at room temperature, it was vacuum filtered. The filtrate was evaporated to dryness and the residue was added to 40 ml of an aqueous 10% potassium carbonate solution and 40 ml of water. The mixture was stirred for 14 hours and another 60 ml of the potassium carbonate solution and 10 ml of water were added. The mixture was stirred for one hour and was then filtered. The filtrate was washed with ethyl acetate and the aqueous phase was acidified with acid potassium sulfate and was extracted with ethyl acetate. The organic extracts were washed with an aqueous saturated sodium chloride solution, dried over sodium sulfate and evaporated to dryness to obtain 6.8 g of a resin. The resin was dissolved in 42 ml of ethyl acetate and 9.1 g of natural quinine were added to the solution at 45° C. The mixtures stood for 20 hours at room temperature and was vacuum filtered and the precipitate was crystallized from ethyl acetate-aqueous ethanol obtain the quinine salt of the acid melting at 233°C and having a specific rotation $[\alpha]_D^{20} = -170.5°$ ($c=1\%$ in methanol).

The said quinine salt was dissolved in 30 ml of absolute or-and 40 ml of an aqueous 10% potassium carbonate solution and 200 ml of water were added thereto. The mixture was vacuum filtered and the filtrate was washed with ethyl acetate. The aqueous phase was acidified with acid potassium sulfate and was extracted with ethyl acetate. The organic extracts were washed with an aqueous solution saturated with sodium chloride, dried over sodium sulfate and evaporated to dryness to obtain 3.24 g of αR-tert.butoxycarboxamido-p-hydroxyphenylacetic acid in the form of a solvated amorphous solid. Theoretical acid No. of 210 (found 189). The product melted at 125°–130°C and had a specific rotation $[\alpha]_D^{20} = 135°$ ($c=1\%$ in ethanol) or 150° for the desolvated product.

EXAMPLE 2

[2′R, 6R, 7R]
7-(α-amino-p-hydroxyphenylacetamido)-3-isopropyl-3-cepheme-4-carboxylic acid STEP A: tert.butyl
2-chloro-2,3-epoxy-3-isopropyl-butanoate A solution of 122 g of potassium tert.-butylate in 720 ml of tetrahydrofuran was added at −20°C with stirring under an inert atmosphere to a mixture of 95 g of methyl isopropyl ketone and 185 g of tert.butyl dichloroacetate and after returning the temperature to room temperature, the mixture was stirred for 2 hours. The mixture was poured into ice water and the mixture was stirred and the organic phase was separated. The organic phase was washed with aqueous sodium chloride solution, dried over magnesium sulfate, passed through vegetable charcoal and concentrated to dryness to obtain 230.4 g of tert.butyl 2-chloro-2,3-epoxy-3-isopropyl-butanoate.

STEP B: tert,butyl 3-isopropyl-2-oxo-3-butenoate 118 g of anhydrous lithium bromide were added under an inert atmosphere to a mixture of 117.5 g of tert.butyl 2-chloro-2,3-epoxy-3-isopropyl-butanoate and 18.5 g of lithium carbonate in 1.15 liters of hexamethylphosphonotriamide cooled to 5°C and after the temperature was returned to room temperature, the mixture was stirred under a nitrogen atmosphere for 48 hours. 500 ml of distilled water were added thereto and the mixture was poured into an ampoule containing a mixture of water-petroleum ether (9-1). The mixture was decanted and the aqueous phase was extracted with petroleum ether. The combined ether phases were washed with water, dried over magnesium sulfate and the petroleum ether was evaporated under reduced pressure to obtain 84.6 g of tert.-butyl 3-isopropyl-2-oxo-3-butenoate.

STEP C: threo and erythro isomers of
2-(α-methoxycarbonyl-α-phthalimidomethyl)-4-tert-butoxycarbonyl-5-isopropyl-2,3-di-hydro-1,3-thiazine 95 g of the threo and erythro isomers of thioaminal of methyl phthalimidomalonaldehyde hydrochloride were added to a solution of 84.4 g of the product of Step B in 420 ml of ethanol cooled to −20°C and while holding the temperature at −20°C, 66 ml of a solution of 40 parts by volume of pyridine in 100 parts by volume of ethanol were added thereto. The mixture stood for 2 hours at room temperature and after 80 ml of water were added, the mixture was cooled on an ice bath for 45 minutes. The mixture was vacuum filtered and the recovered precipitate was washed with a 1-1 ethanol-water mixture and then was empasted with petroleum ether and dried to obtain 108.1 g of the threo and erythro isomers of 2-(α-methoxycarbonyl-α-phthalimidomethyl)-4-tertibutoxycarbonyl-5-isopropyl-2,3-dihydro-1,3-thiazine which was used as is for the next step.

STEP D: threo and erythro isomers of
2-(α-methoxycarbonyl-α-aminomethyl)-4-tertibutoxycarbonyl-5-isopropyl-2,3-dihydro-1,3-thiazine 55 ml of a solution of 2 M hydrazine hydrate in dimethylformamide were added to a solution of 46.1 g of threo and erythro isomers of the product of Step C in 46 ml of chloroform cooled to 0°C and the mixture was stirred for 1 hour at room temperature. Then, 600 ml of ether and 30 ml of acetic acid were added to the mixture which was then allowed to stand for 1 hour. The mixture was filtered and the filter was rinsed with ether. The filtrate was added to 400 ml of a saturated aqueous sodium bicarbonate solution and the mixture was stirred for 10 minutes and decanted. The organic phase was washed with water. The aqueous phase was washed with ether and the combined organic phases were dried over magnesium sulfate, vacuum filtered and the solvent was evaporated under reduced pressure to obtain threo and erythro isomer mixture of 2-(α-methoxycarbonyl-α-aminomethyl)-4-tert.-butoxycarbonyl-5-isopropyl-2,3-dihydro-1,3-thiazine.

STEP E: threo isomer of
2-(α-carboxy-α-aminomethyl)-4-tert.-butoxycarbonyl-5-isopropyl-2,3-dihydro-1,3-thiazine The threo and erythro isomers of Step D were dissolved in 100 ml of acetone with stirring under a nitrogen atmosphere and after cooling the solution to 0°C, 100 ml of N sodium hydroxide solution were added thereto. After standing for 20 minutes, 6.3 ml of acetic acid were added to the mixture which was then stirred for 1 hour and vacuum filtered. The precipitate was empasted with ether and filtered under a maximum vacuum. The product was dried under reduced pressure and the dried residue was ground and then empasted with acetone and then ether. The product was dried under reduced pressure to obtain 13.2 g of the threo isomer of 2-(α-carboxy-α-aminomethyl)-4-tert.butoxycarbonyl-5-isopropyl-2,3-dihydro-1,3-thiazine in the form of white crystals melting towards 150°C with decomposition.

STEP F: threo isomer of 2-(α-carboxy-α-tritylaminomethyl)-4-tert.butoxycarbonyl-5-isopropyl-2,3-dihydro-1,3-thiazine A solution of 10.7 g of trityl chloride in 70 ml of chloroform was added with stirring under a nitrogen atmosphere to a solution of 11.1 g of the threo isomer of Step E in 140 ml of chloroform and 10.8 ml of triethylamine cooled to −50°C and the mixture was stirred for 30 minutes at −50°C. The mixture was returned to room temperature and was evaporated to dryness. The residue was dissolved in 170 ml of methanol and 21.5 ml of 2 N hydrochloric acid were added thereto. The mixture was stirred for 15 minutes and was vacuum filtered. The precipitate was washed with methanol, then with isopropyl ether and dried to obtain 9.1 g of the threo isomer of 2-(α-carboxy-α-tritylaminomethyl)-4-tert.butoxycarbonyl-5-isopropyl-2,3-dihydro-1,3-thiazine in the form of colorless crystals melting towards 180°C with decomposition.

STEP G: tert.butyl dl cis 7-tritylamino-3-isopropyl-3-cepheme-4-carboxylate

A mixture of 14.9 g of the threo isomer of Step F in 15 ml of chloroform and 1500 ml of nitromethane was cooled to 0°C and a solution of 6.4 g of dicyclohexyldicarbodiimide in 52 ml of chloroform was added thereto. After returning to room temperature, 27 ml of pyridine were added to the mixture which was stirred for 15 hours under nitrogen. The reaction mixture was vacuum filtered to remove insolubles and the filter was washed with ether. The combined filtrates were evaporated to dryness and the residue was taken up in 60 ml of methylene chloride. The mixture was vacuum filtered and the filtrate was evaporated to dryness. The product was then suspended in 95 ml of ethanol and after stirring, the resulting precipitate was recovered by vacuum filtration to obtain 8.3 g of tert. butyl dl cis 7-tritylamino-3-isopropyl-3-cepheme-4-carboxylate.

STEP H: tert.butyl dl cis 7-amino-3-isopropyl-3-cepheme-4-carboxylate

A solution of 7.57 g of the ester of Step G in 14 ml of chloroform, 8.4 ml of methanol and 2.8 ml of 10 N hydrochloric acid in ethanol stood for 20 minutes and 84 ml of ether were added thereto. The mixture was vacuum filtered and the crystals were washed with ether and dried to obtain 4.6 g of tert.butyl dl cis 7-amino-3-isopropyl-3-cepheme-4-carboxylate hydrochloride. 3 g of the said hydrochloride were added to 20 ml of methylene chloride and 25 ml of a 10% aqueous sodium bicarbonate solution with stirring and the organic phase was decanted. The aqueous phase was extracted with methylene chloride and the combined organic phases were dried over magnesium sulfate and vacuum filtered. The filter was washed with methylene chloride and the filtrate was evaporated to dryness to obtain 2.54 g of tert.butyl dl cis 7-amino-3-isopropyl-3-cepheme-4-carboxylate in the form of colorless crystals melting at 114°C.

STEP I. Resolution

A mixture of 2.38 g of the ester of Step H and 1.3 g of D(−) tartaric acid in 8 ml of methanol was heated to reflux and after returning the temperature to 25°C, the mixture was vacuum filtered. The precipitate was washed with a 1-1 mixture of methanol and ether and then with ether and dried to obtain 1.394 g of the tartrate of tert.butyl dl cis 7-amino-3-isopropyl-3-cepheme-4-carboxylate. The said 1.394 g were stirred with 15 ml of a 10% aqueous sodium bicarbonate solution and 15 ml of methylene chloride and the organic phase was decanted. The aqueous phase was extracted with methylene chloride and the combined organic phases were dried over magnesium sulfate and evaporated to dryness to obtain 919 mg of tert.butyl [6R, 7R] 7-amino-3-isopropyl-3-cepheme-4-carboxylate in the form of colorless crystals melting at 132°C and having a specific rotation $[\alpha]_D^{20} = + 47.5°$ ($c = 0.6\%$ in chloroform).

STEP J: Tert.butyl 7-(αR-tertbutoxycarboxamido-p-hydroxyphenylacetamido)-3-isopropyl-3-cepheme-4-carboxylate 1.3 g of dicyclohexylcarbodiimide were added to a solution of 3.3 g of αR-tertbutoxycarboxamido-p-hydroxyphenylacetic acid in 20 ml of chloroform cooled to 0°C and after stirring the mixture for 10 minutes, 1 ml of pyridine and 1.5 g of tert.butyl [6R, 7R] 7-amino-3-isopropyl-3-cepheme-4-carboxylate were added thereto. The mixture was stirred for 1½ hours at room temperature and was then vacuum filtered. The filtrate was evaporated to dryness and the residue was dissolved in ether. The ether solution was washed with dilute hydrochloric acid, with water, with a 10% aqueous sodium bicarbonate solution and dried over magnesium sulfate. The solution was filtered through a silica column and the other was evaporated to obtain tert.butyl 7-(αR-tertbutoxycarboxamido-p-hydroxyphenylacetamido)-3-isopropyl-3-cepheme-4-carboxylate in the form of a thick oil.

STEP K: [2'R, 6R, 7R] 7-(α-amino-p-hydroxyphenylacetamido)-3-isopropyl-3-cepheme-4-carboxylic acid The oil of Step J was added to 30 ml of trifluoroacetic acid and after stirring the mixture for 15 minutes at room temperature, the major part of trifluoroacetic acid was evaporated under reduced pressure. Isopropyl ether was added thereto and the precipitate recovered by vacuum filtration was dissolved in water. The resulting solution was added to 8 ml of an about molar solution of an anionic resin of the secondary amine type in the acetate form in methyl isobutyl ketone and the mixture was stirred for 15 minutes. The resin was decanted and the aqueous phase was concentrated under reduced pressure. The residue was triturated with acetone and the crystals were vacuum filtered to obtain 1.3 g of [2'R, 6R, 7R] 7-(α-amino-p-hydroxyphenylacetamido)-3-isopropyl-3-cepheme-4-carboxylic acid in the form of colorless crystals melting at 220°C (with decomposition) and a specific rotation $[\alpha]_D^{20} = + 114°$ ($c=0.5\%$ in 0.1 N hydrochloric acid).

Analysis: $C_{18}H_{21}N_3O_5S$, Calculated: %C; 55.24, %H; 5.41, %N; 10.74 %S; 8.18, Found: %C; 55.6, %H; 5.5,

%N; 11.0, %S; 8.1.

EXAMPLE 3

[6R, 7R]
7-(4-phenyl-3-sydnoneacetamido)-3-isopropyl-3-cepheme-4-carboxylic acid 1 g of dicyclohexylcarbodiimide was added to a solution of 1.3 g of 4-phenyl-3-sydnoneacetic acid [J. Chem. Soc., (1963), p. 701] in 10 ml of nitromethane and after stirring for 15 minutes, the mixture was vacuum filtered. 0.75 g of tertbutyl [6R, 7R] 7-amino-3-isopropyl-3-cepheme-4-carboxylate was added to the filtrate and after stirring the mixture for 1 hour at room temperature, it was evaporated to dryness under reduced pressure. The residue was taken up in ethyl acetate and the solution was cooled with a sodium bicarbonate solution, with dilute hydrochloric acid and with water. The solution was then dried over magnesium sulfate and was evaporated to dryness under reduced pressure. The residue was chromatographed over silica with a 1-1 methylene chloride-ether mixture as eluant to obtain an oil which was dissolved in 10 ml of trifluoroacetic acid. The solution was stirred for 15 minutes and then evaporated to dryness under reduced pressure. The residue was added to ether and the precipitate obtained was dissolved in methanol containing 30% of water. A large excess of triethylamine was added thereto and the precipitate was removed by vacuum filtration. The filtrate was acidified with dilute hydrochloric acid and the precipitate was recovered by vacuum filtration and was washed with water and ether to obtain 0.5 g of [6R, 7R] 7-(4-phenyl-3-sydnoneacetamido)-3-isopropyl-3-cepheme-4-carboxylic acid in the form of colorless crystals melting at 220°C (with decomposition).

Analysis: $C_{20}H_{20}N_4O_6S$. Calculated: %C; 54.05, %H; 4.54, %N; 12.61, %S; 7.21, Found: %C; 54.3, %H; 4.7, %N; 12.5, %S; 7.1.

EXAMPLE 4

Diethylamine salt of [6R, 7R] 7-(3-sydnoneacetamido)-3-isopropyl-3-cepheme-4-carboxylic acid Using the procedure of Example 3, 1.7 g of 3-sydnoneacetic acid was reacted with diethylamine without the acidification step to obtain the diethylamine salt of [6R, 7R] 7-(3-sydnoneacetamido)-3-isopropyl-3-cephene-4-carboxylic acid melting at 180°C.

EXAMPLE 5 dl cis 7-amino-3-isopropyl-3-cepheme-4-carboxylic aicd

A mixture of 541 mg of tert.butyl 7-tritylamino-3-isopropyl-3-cepheme-4-carboxylate in 11 ml of nitromethane was cooled on an ice bath and a current of gaseous hydrochloric acid was passed therethrough for 15 minutes. The mixture was evaporated to dryness and the residue was taken up in ether. The ether solution was vacuum filtered and the residue was washed with ether and dried. The residue was taken up in 1 ml of water and the pH was adjusted to 4 by addition of pyridine. The mixture was vacuum filtered and the crystals were washed with water, with acetone and then with ether and dried to obtain 204 mg of dl cis 7-amino-3-isopropyl-3-cepheme-4-carboxylic acid in the form of colorless crystals melting towards 230°C with decomposition.

EXAMPLE 6

Preparations suitable for injections were prepared from 500 mg of [2'R, 6R, 7R] 7-(α-amino-p-hydroxyphenylacetamino)-3-isopropyl-3-cepheme-4-carboxylic acid or [6R, 7R] 7-(4-phenyl-3-sydnoneacetamido)-3-isopropyl-3-cepheme-4-carboxylic acid and sufficient sterile aqueous excipitate to make a total of 5 ml. Gelules were prepared from 250 mg of [2'R, 6R, 7R] 7-(α-amino-p-hydroxyphenylacetamido)-3-isopropyl-3-cepheme-4-carboxylic acid and sufficient excipitate to obtain a final gelule weighing 400 mg.

PHARMACOLOGICAL STUDY

A. Antibacterial Activity in vitro

The antibacterial activity of [2'R, 6R, 7R] 7-(α-amino-p-hydroxyphenylacetamido)-3-isopropyl-3-cepheme-4-carboxylic acid (Product A) and [6R, 7R] 7-(4-phenyl-3-sydnoneacetamido)-3-isopropyl-3-cepheme-4-carboxylic acid (Product B) was determined by dilution method in liquid media. A series of tubes in which equal quantities of a nutritive media was placed were prepared and increasing amounts of the test product were distributed to the tubes. Then, each tube was seeded with a bacterial stock and after incubation for 24, 48 or 72 hours in an oven at 37°C, the growth inhibition was determined by transillumination to ascertain the minimum inhibitory concentrated (MIC) expressed as mcg/ml. The nutritive media was a liquid media with a pH of 7 and the results are reported in Table I.

TABLE

| Bacteria | Product A 24 H | Product A 48 H | Product A 72 H | Product B 24 H | Product B 48 H |
|---|---|---|---|---|---|
| Bacillus subtilis | 0.1 | 0.1 | 0.1 | <0.05 | 0.1 |
| Staphylococcus aureus | | | | | |
| - Oxford U.C. 1061 | 0.2 | 0.6 | 2 | 0.4 | 2 |
| - Penicillin-sensible | | | | | |
| U.C. 1128 | 1 | 1 | 1 | 1 | 2 |
| - Penicillin-resistant | | | | | |
| 54 146 | 1 | 2 | 2 | — | — |
| Streptococcus | | | | | |
| hemolyticus | 1 | 1 | 1 | 50 | >50 |
| Streptococcus faecalis | 10 | 40 | >40 | 5 | 40 |
| Escherichia coli | | | | | |
| U.C. 1020 | 40 | 100 | 100 | >100 | — |
| U.C. 1261 | 20 | 40 | 40 | >100 | — |
| Salmonella typhi | | | | | |
| Scr 8 | 5 | 10 | 20 | — | — |

Another test was conducted to compare product A and cephalexin in the same test with different staphylococcus and streptococcus strains and the results are reported in Table II.

TABLE II

| Bacteria | Product A 24 H | Product A 48 H | Cephalexin 24 H | Cephalexin 48 H |
|---|---|---|---|---|
| Staphylococcus aureus | | | | |
| G III L 14 | 0.2 | 0.4 | 2 | 2 |
| G II L 8 | 0.2 | 0.4 | 2 | 3 |
| 1583 | 0.4 | 1 | 3 | 10 |
| 8371 | 0.4 | 1 | 2 | 3 |
| 9482 (2) | 0.4 | 1 | 2 | 3 |
| 4546 | 0.5 | 2 | 1 | 3 |
| 9729 (2) | 1 | 1 | 5 | 5 |
| 9973 | 1 | 2 | 2 | 3 |
| 889 | 2 | 3 | 5 | 20 |
| Streptococcus pyogenes | | | | |
| (group A) | 0.02 | 0.02 | 0.4 | 0.4 |
| Streptococcus faecalis | | | | |
| 5432 | 20 | 20 | 60 | >100 |

TABLE II-continued

| Bacteria | Product A 24 H | Product A 48 H | Cephalexin 24 H | Cephalexin 48 H |
|---|---|---|---|---|
| *Escherichia Coli* 9927 | 40 | 60 | 100 | 100 |

B. Bactericidal Activity

The bactericidal activity of product A was determined from the number of living germs subsisting after treatment in liquid media with increasing amounts of the product. The cultures were placed in the tubes from the preceding test for about 48 hours. The samples were then transplanted to Petrie dishes 10cm in diameter with a solid gelose media with a pH of 7.4. A steady sample was withdrawn from the last tube having growth and the tubes watched to observe the growth by transillumination. After 48 hours of culture, the microbial growth was noted and the results are reported in Table III. ++++ indicates total growth and − indicates the absence of colonies.

TABLE III

| Concentrations mcg/cm³ | 1 | 2 | 3 | 5 | 10 | 20 | 30 | 40 | 50 | 60 | 80 | 100 | 200 |
|---|---|---|---|---|---|---|---|---|---|---|---|---|---|
| Souches | | | | | | | | | | | | | |
| *Staphylococcus aureus* | | | | | | | | | | | | | |
| 54 146 | ++++ | 5 cd. | | 3 col. | − | | | | | | | | |
| ATCC 6 538 | | ++++ | + | 9 col. | 30 col. | | | | | | | | |
| 4 546 | ++++ | − | | | | | | | | | | | |
| 8 514 | ++++ | + | − | − | | | | | | | | | |
| 9 561 | | ++++ | 32 col. | − | 4 col. | 6 col. | | 5 col. | | | | | |
| *Streptococcus faecalis* | | | | | | | | | | | | | |
| 5 432 | | | | | +++ | − | | − | | | | | |
| *Streptococcus hemolyticus* | | | | | | | | | | | | | |
| 905 | +++ | − | − | − | | | | | | | | | |
| *Escherichia Coli* | | | | | | | | | | | | | |
| T | | | | | | | +++ + | ++++ | − | − | − | − | − |
| 152 | | | | | | | ++++ | − | − | − | − | | |
| 3 019 | | | | | | | ++++ | 16 col. | ++ | − | − | | |
| *Shigella sonnei* | | | | | | | | ++++ | | − | − | | |
| *Klebsiella pneumoniae* | | | | | | | | | | | | | |
| 52 145 | | | | | | | | | | ++++ | − | − | |
| *Proteus mirabilis* | | | | | | | ++++ | 6 col. | − | | | | |

The results of Tables I to III show that the products of the invention have a good activity against pathogenic microorganisms.

C. Antibacterial Activity in Vivo

The activity of product A against a staphylococcus was studied experimentally in mice. Groups of 10 mice with an average weight of about 26 g were infected intraperitoneally with a culture of Staphylococcus aureus 54, 146 in Pasteur nutritive broth diluted 1/3.25 with distilled water. The mice were treated by oral administration of product A in 2 doses, 1 hour and 5 hours after infection. After 7 days, the mortality rate was determined and the results are reported in Table IV.

TABLE IV

| Individual dose in mg | Mortality in 24 H | Mortality in 48 H | No. of mice alive after 7 days |
|---|---|---|---|
| 0 | 10 | | 0 |
| 0.5 | | | 10 |
| 1 | | 1 | 9 |
| 1.5 | | | 10 |

This test shows that product A has a good antibacterial activity against staphylococci.

Various modifications of the products and processes of the invention may be made without departing from the spirit or scope thereof and it should be understood that the invention is to be limited only as defined in the appended claims.

We claim:
1. A compound selected from the group consisting of cephalosporan compounds of the formula

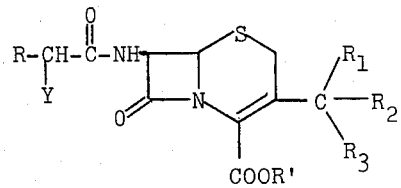

in the form of racemic mixtures or optically active isomers or in form of their cis or trans isomers or mixtures thereof wherein R is phenyl substituted with one hydroxyl, R' is selected from the group consisting of hydrogen and R'', R'' is an ester group easily removable by acid hydrolysis or hydrogenolysis selected from the group consisting of alkyl of of 1 to 6 carbon atoms optionally substituted by at least one chlorine and aralkyl of 7 to 15 carbon atoms, $R_1$ and $R_2$ are alkyl of 1 to 3 carbon atoms, $R_3$ is selected from the group consisting of hydrogen and alkyl of 1 to 3 carbon atoms, Y is selected from the group consisting of amino and Y', Y' is hydrogen and NHCOOZ, Z is straight or branched alkyl of 1 to 5 carbon atoms and their non-toxic, pharmaceutically acceptable addition salts with organic and inorganic acids and bases where appropriate with the proviso that when Y is amino, R' is hydrogen and when Y is amino or NHCOOZ, R is phenyl.

2. A compound of claim 1 wherein R' is hydrogen and Y is selected from the group consisting of hydrogen and amino.

3. A compound of claim 1 wherein R' and $R_3$ are hydrogen, $R_1$ and $R_2$ are methyl and Y is selected from the group consisting of hydrogen and amino.

4. A compound of claim 1 selected from the group consisting of [2R', 6R, 7R] 7-($\alpha$-amino-p-hydroxyphenylacetamido)-3-isopropyl-3-cepheme-4-carboxylic acid and its salts.

* * * * *